United States Patent [19]
Tatsumi et al.

[11] Patent Number: 6,054,305
[45] Date of Patent: Apr. 25, 2000

[54] PYRUVATE ORTHOPHOSPHATE DIKINASE GENE, RECOMBINANT DNA, AND PROCESS FOR PRODUCING PYRUVATE ORTHOPHOSPHATE DIKINASE

[75] Inventors: Hiroki Tatsumi; Naoki Eisaki; Tatsuo Horiuchi; Ayumu Nagahara, all of Chiba, Japan

[73] Assignee: Kikkoman Corporation, Japan

[21] Appl. No.: 08/941,936

[22] Filed: Oct. 1, 1997

[30] Foreign Application Priority Data

Oct. 3, 1996 [JP] Japan .................................. 8-281304

[51] Int. Cl.[7] .............................. C12N 9/12; C12N 15/54; C12N 15/63; C12N 1/21
[52] U.S. Cl. ..................... 435/194; 536/23.1; 536/23.2; 435/71.2; 435/252.3; 435/252.33; 435/320.1
[58] Field of Search ................... 536/23.1, 23.2; 435/71.2, 194, 252.3, 252.33, 320.1

[56] References Cited

FOREIGN PATENT DOCUMENTS

| | | |
|---|---|---|
| 212781 | 12/1983 | Japan . |
| 12300 | 1/1986 | Japan . |
| 168375 | 7/1996 | Japan . |
| 205861 | 8/1996 | Japan . |

OTHER PUBLICATIONS

E. Saavedra–Lira et al., "Cloning and Sequence Determination of the Gene Coding for the Pyruvate Phosphate Dikinase of Entamoeba histolytica", Gene 142(2): 249–251, 1994.

L. Nevalainen et al., "Sequence of a Giardia lamblia Gene Coding for the Glycolytic Enayme, Pyruvate Phosphate Dikinase", Mol. Biochem. Parasitol. 77(2): 217–223, 1996.

Kikkoman, "Pyruvate–Orthophosphate–Dikinase and Production Thereof", Derwent–Biotechnol. Absts. 15(21): 104, ABst. No. 96–12552 Jul. 1996.

Sakakibara et al., 116th Annual Meeting of Pharmaceutical Society of Japan, *Lecture Summary 4*, p. 154 (1996).

Hoffman et al., "A ten–minute DNA preparation from yeast efficiently releases autonomous plasmids for transformation of *Escherichia coli*," *Gene* 57: 267–272 (1987).

Morrison, "Transformation and Preservation of Competent Bacterial Cells by Freezing," *Methods in Enzymology* 68:326–331 (1979).

Hohn, "In Vitro Packaging of λ and Cosmid DNA," *Methods in Enzymology* 68: 299–309 (1979).

Messing, "New M13 Vectors for Cloning," *Methods in Enzymology* 101: 20–78 (1983).

Niersbach et al., "Cloning and nucleotide sequence of the *Escherichia coli* K–12 ppsA gene, encoding PEP synthase," *Mol. Gen. Genet.* 2341: 332–336 (1992).

*Primary Examiner*—Rebecca E. Prouty
*Attorney, Agent, or Firm*—Medlen & Carroll, LLP

[57] ABSTRACT

Disclosed are a pyruvate orthophosphate dikinase gene coding for a polypeptide containing the amino acid sequence of SEQ ID NO:1 or an amino acid sequence where in said amino acid sequence one or more amino acids are added, deleted or substituted and bringing about the activity of pyruvate orthophosphate dikinase; recombinant DNA having the pyruvate orthophosphate dikinase gene integrated in vector DNA; and a process for producing pyruvate orthophosphate dikinase, which comprises culturing a microorganism belonging to the genus Escherichia carrying the above recombinant DNA in a medium, and recovering pyruvate orthophosphate dikinase from the resulting culture. The pyruvate orthophosphate dikinase gene and a process for producing pyruvate orthophosphate dikinase are provided.

21 Claims, 1 Drawing Sheet

Ap. β-lactamase gene
B, BamHI
Bg, BglII
H, HindIII

PYRUVATE ORTHOPHOSPHATE DIKINASE GENE, RECOMBINANT DNA, AND PROCESS FOR PRODUCING PYRUVATE ORTHOPHOSPHATE DIKINASE

FIELD OF THE INVENTION

The present invention relates to a pyruvate orthophosphate dikinase gene, recombinant DNA containing said gene, and a process for producing pyruvate orthophosphate dikinase.

BACKGROUND OF THE INVENTION

Pyruvate orthophosphate dikinase (referred to hereinafter as "PPDK") is an enzyme which catalyzes a reaction for forming adenosine 5'-triphosphate (ATP), pyruvic acid and phosphoric acid from adenosine 5'-monophosphate (AMP), phosphoenol pyruvic acid and pyrophosphoric acid. This enzyme is used for quantification of, for example, pyrophosphoric acid (Japanese Patent Appln. LOP Publication No. 12300/86). Further, in reference to bioluminescence method, this enzyme is utilized to maintain a high level stable emission without decaying for a long period of time (Kashiwabara et al., 116th Anneal Meeting of Pharmaceutical Society of Japan, Lecture Summary 4, page 154).

Eisaki et al. found a novel PPDK in a strain belonging to the genus Microbispora, which is stable in storage in a low-temperature range and resistant to freezing and thawing (Japanese Patent Appln. LOP Publication No. 168375/86). However, a problem has been that only a small amount of PPDK can be produced when this strain is cultured to produce the enzyme. Another problem is that this strain must be cultured for about 3 days during which contamination with other microorganisms can easily occur.

SUMMARY OF THE INVENTION

The object of the present invention is to provide a PPDK gene, recombinant DNA containing the gene and a process for producing PPDK.

The present inventors successfully isolated a PPDK gene from a microorganism belonging to the genus Microbispora to complete the present invention.

That is, the present invention relates to a PPDK gene coding for a polypeptide containing the amino acid sequence of SEQ ID NO:1 or an amino acid sequence where one or more amino acids are added, deleted or substituted in SEQ ID NO:1 and bringing about the PPDK activity.

What is meant by the phrase "amino acid sequence where one or more amino acids are added, deleted or substituted," is that in as much as the desired PPDK activity can be obtained, some amino acids in the amino acid sequence of SEQ ID NO:1 may be added, deleted or substituted. For example, if the desired PPDK activity is obtained even if methionine at the 1-position is deleted from the amino acid sequence of SEQ ID NO:1, a sequence with such a deletion is intended to fall under the scope of the present invention.

Further, the present invention relates to recombinant DNA having said PPDK gene integrated in vector DNA.

Further, the present invention relates to a process for producing PPDK, which comprises culturing a microorganism belonging to the genus Escherichia carrying the recombinant DNA in a medium, and recovering PPDK from the resulting culture.

DETAILED DESCRIPTION OF THE INVENTION

Figure 1:
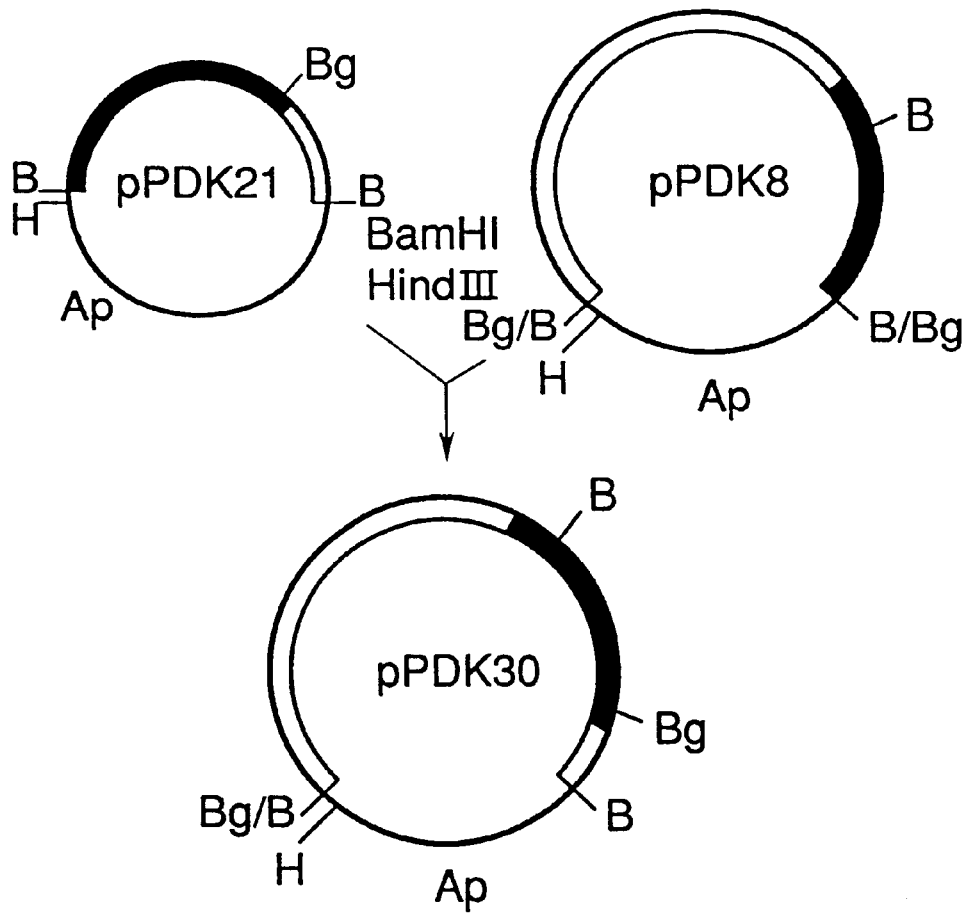
FIG. 1 shows the construction of plasmid pPDK30.
Figure 1:
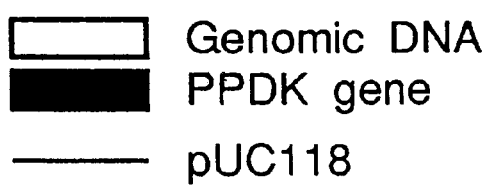

Hereinafter, described in detail are a method of isolating a gene (i.e. "PPDK gene") coding for PPDK of the present invention (referred to hereinafter as "the present enzyme"), a process of producing the present enzyme by use of a microorganism carrying recombinant DNA having said gene integrated in it, and a method of measuring the activity of the present enzyme.

1. Isolation of the PPDK Gene

The PPDK gene is obtained, for example, by cloning a wild-type gene derived from genomic DNA or cDNA from a microorganism having the ability to produce the present enzyme. Alternatively, said gene can also be amplified by polymerase chain reaction (referred to hereinafter as "PCR") using genomic DNA or cDNA as a template and a primer synthesized based on the amino acid sequence of the present enzyme. Further, said gene can also be constructed by chemical synthesis means.

Hereinafter, a method of isolating the PPDK gene is described by reference to a method of cloning the PPDK gene from a genomic DNA library of a microorganism belonging to the genus Microbispora having the ability to produce the present enzyme (referred to hereinafter as "genomic DNA library").

(1) Preparation of the Genomic DNA Library

The microorganism belonging to the genus Microbispora having the ability to produce the present enzyme includes, for example, *Microbispora thermorosea* (*Microbispora thermorosea* IFO14047), etc. Said microorganism that has been cultured in a medium designated by IFO (IFO medium No. 231), for example, can be used.

The method of extracting genomic DNA from said microorganism may be any of the known methods. Specifically, such methods are those described in the Examples below, or the method of Hoffman et al. (Gene, 57, 267–272, 1987), etc.

The resulting genomic DNA is completely digested with suitable restriction enzymes to give fragments of the genomic DNA. Then, the fragments are subjected to conventional agarose gel electrophoresis and a gel containing a fragment of target size is cleaved off. Then, the DNA fragment in the cleaved gel is purified using, for example, GENE CLEAN II (Funakoshi), etc. to obtain recombinant DNA which is then used for the transformation or transduction of host cells whereby a genomic DNA library is prepared.

The vector DNA into which the DNA fragment is inserted may be any DNA capable of replication in host cells; examples are plasmid DNA, bacteriophage DNA, etc. If the host cell is *E. coli*, plasmid pUC118 (Takara Shuzo), pBluescript SK+ (Stratagene), pMAL-C2 (New England Labs), pGEX-5X-1 (Pharmacia), pXa1 (Boehringer Mannheim), etc. can be used. Besides, temperature-sensitive bacteriophage (FERM BP-133, Japanese Patent Appln. LOP Publication No. 212781/83), etc. can also be used.

The host cells may be either eukaryotic or prokaryotic cells. The eukaryotic cells include cells from animals, plants, insects, yeast, etc. and the prokaryotic cells include *E. coli, Bacillus subtilis*, Actinomyces, etc. Specifically, microorganisms belonging to the genus Escherichia, e.g. *E. coli* TG1 (Amersham), XL1-Blue (Stratagene), JM109 (Takara Shuzo), HB101 (ATCC33694), etc. can be used preferably.

The recombinant DNA can be used for the transformation or transduction of host cells such as *E. coli* TG1, etc. to give a recombinant microorganism carrying a genomic DNA fragment containing various genes.

In the present invention, transformation can be effected by, for example, the D. M. Morrison method (Methods in Enzymology, 68, 326–331, 1979) and transduction by, for example, the B. Hohn method (Methods in Enzymology, 68, 299–309, 1979).

In addition to the method of inserting a gene into genomic DNA in host cells described above, homologous recombination can also be used in the present invention to introduce a gene into the host cells. Specifically, the introduction of a gene by homologous recombination can be effected by, for example, the microinjection method, etc.

(2) Isolation of the PPKD Gene

For screening the recombinant microorganism carrying the PPDK gene from the genomic DNA library prepared above, colony hybridization (Current Protocols in Molecular Biology (WILEY Interscience, 1989)), plaque hybridization, etc. may be carried out using a DNA fragment that corresponds to a part of the PPDK gene.

The DNA fragment used as a probe can be prepared using the PCR method. First, an oligonucleotide is synthesized based on the N-terminal amino acid sequence of the present enzyme and it is used as a 5'-primer. Then, an oligonucleotide is synthesized based on the amino acid sequence of a highly conserved region among conventionally known PPDKs and it is used as a 3'-primer. With respect to the conventionally known PPDKs, mention can be made of those derived from *Clostridium symbiosum*, *Zea mays* and *Flaveria trinervia*. In addition, phosphoenol pyruvate synthase and enzyme I derived from *E. coli* are known to have high homology to PPDK, so it is also possible to synthesize a primer on the basis of the amino acid sequences of these enzymes.

PCR is carried out using these oligonucleotides as PCR primers and the genomic DNA from *Microbispora thermorosea* as a template whereby a DNA fragment corresponding to a part of the PPDK gene can be amplified. The codons used for synthesis of the PCR primers are preferably those frequently used in microorganisms belonging to the genus Microbispora.

The probe can be labeled with non-radioactive substances such as digoxigenin (Boehringer Mannheim), etc. or with radioisotopes such as [$\gamma$-$^{32}$P]-ATP (Amersham Japan), etc.

To obtain purified recombinant DNA from the recombinant microorganism carrying the PPDK gene, QIAGEN Plasmid Mini Kit (Funakoshi) and methods such as cesium chloride density-gradient ultracentrifugation, etc. may be used.

(3) Analysis of the Gene

The nucleotide sequence of the PPDK gene integrated in the recombinant DNA obtained above can be determined by the dideoxy method (Methods in Enzymology, 101, 20–78, 1983).

The amino acid sequence of the present enzyme is deduced from the nucleotide sequence of the determined nucleotide sequence of the PPDK gene. This amino acid sequence is shown in SEQ ID NO:1.

In the amino acid sequence of SEQ ID NO:1, one or more amino acids may be added, deleted or substituted so long as the PPDK activity is not lost. The present invention encompasses every gene coding for a polypeptide whose amino acid sequence has been mutated without losing the PPDK activity.

The above mutant PPDK gene is obtained by mutating the wild-type gene. The method of mutating the gene involves contacting the wild-type gene with mutagenic chemicals, specifically hydroxylamine, nitrite, sulfite, 5-bromouracil etc. Besides, a variety of methods such as ultraviolet ray irradiation, cassette mutagenesis, site-directed mutagenesis using the PCR method, etc. can be used. Further, chemically synthesized DNA can also be annealed to construct the mutant gene mutated in a desired site.

2. Production of the Present Enzyme by the Recombinant Microorganism

The present enzyme can be produced by culturing the recombinant microorganism carrying the recombinant DNA in which the PPDK gene has been integrated downstream from a suitable promoter.

Although, the culture method may be carried out using a conventional solid medium, culture in a liquid medium is preferred.

To culture the recombinant microorganism, use is made of a medium prepared by adding one or more inorganic salts such as potassium dihydrogen phosphate, dipotassium hydrogen phosphate, magnesium sulfate, ferric chloride, ferric sulfate, manganese sulfate, etc. to one or more nitrogen sources selected from yeast extract, peptone, meat extract, corn steep liquor, exudates from soybean or wheat bran, etc. If necessary saccharides, vitamins, etc. are added to the medium. In addition, isopropyl-$\beta$-thiogalactoside (IPTG), etc. may be added to the medium if necessary to induce the expression of the PPDK gene.

The initial pH value of the medium is preferably adjusted in the range of 7 to 9. Culture is carried out at 25 to 42° C., preferably 37° C. or thereabout, for 6 to 24 hours, by stirring culture under aeration, shake culture, stationary culture, etc.

After culture, conventional enzyme recovery means can be used to recover the present enzyme from the culture. That is, the microorganism is disrupted by lysis treatment with an enzyme such as lysozyme, etc., or by ultrasonication, grinding, etc. to release the present enzyme from the microorganism. Then, insolubles are removed by filtration or centrifugation whereby a crude enzyme solution containing the present enzyme is obtained. In the present invention, said crude enzyme solution itself can be used as a preparation of the present enzyme or may be further purified using the following purification means.

To further purify the present enzyme from the crude enzyme, conventional protein purification methods can be used. Specifically, methods such as salting out with ammonium sulfate, organic solvent precipitation, ion-exchange chromatography, hydrophobic chromatography, gel filtration chromatography, absorption chromatography, affinity chromatography, electrophoresis, etc. are used solely or in combination.

The physicochemical properties of the present enzyme produced by genetic engineering means are completely the same as those of PPDK produced by microorganisms belonging to the genus Microbispora as the DNA donor.

3. Method of Measuring the Activity of the Present Enzyme

Hereinafter, the method of measuring the activity of the present enzyme is described. In this method, ATP is formed by the catalytic reaction of the present enzyme and then quantified using emission.

First, 180 $\mu$l of 50 mM Bis-Tris propane buffer, pH 6.8 containing 3 mM magnesium sulfate, 25 mM ammonium sulfate, 2 mM mercaptoethanol, 2 mM pyrophosphoric acid, 2 mM phosphoenol pyruvic acid and 0.1 mM AMP is introduced into a micro-tube and heated to 37° C. Then, 20 $\mu$l solution of the present enzyme is introduced and reacted for 15 minutes, and then boiled for 3 minutes in boiling water to stop the reaction. 50 $\mu$l diluent of this reaction solution is introduced into a test tube, and 50 $\mu$l solution of "Lucifer LU" (Kikkoman) is dripped into it and the emission is measured. Separately, a calibration graph is prepared by plotting emission against concentration where standard ATP solutions of known concentration are used. This graph is used to determine the amount (in $\mu$ mol) of ATP formed per minute at 37° C., and this amount is assumed to be the activity of the enzyme solution. The amount of the enzyme causing formation of $1\mu$ mol ATP per minute at 37° C. is assumed to be 1 U.

EXAMPLES

Hereinafter, the present invention is described in more detail by reference to the Examples, which, however, are not intended to limit the scope of the invention.
(1) Preparation of Genomic DNA Genomic DNA was prepared in the following manner: *Microbispora thermorosea* (*Microbispora thermorosea* IFO14047) was inoculated into 50 ml medium designated by IFO (IFO medium No. 231) and cultured at 45° C. for 72 hours under shaking. The microorganism was then recovered by centrifugation. The resulting microorganism, 500 mg, was suspended in 5 ml solution for disruption [2 mg/ml lysozyme, 25 mM disodium ethylenediaminetetraacetate (EDTA), 25 mM Tris [tris(hydroxymethyl)aminomethane]-HCl, 0.3 M sucrose, pH 8.3] and transferred to a test tube and the microorganism was lysed at 37° C. for 30 minutes with occasional shaking. Then, 250 $\mu$l of 10% sodium dodecyl sulfate (SDS) and 25 $\mu$l proteinase K solution (20 mg/ml) were added to it and the microorganism was further lysed at 37° C. for 60 minutes. Then, 800 $\mu$l of 5 M NaCl, 640 $\mu$l of 10% CTAB (cetyltrimethylammonium bromide)/ 0.7 M NaCl was added and the microorganism was left at 65° C. for 10 minutes.

Thereafter, chloroform extraction, isopropanol precipitation and ethanol precipitation were carried out in a usual manner to obtain 100 $\mu$g of genomic DNA.
(2) Southern Blot Analysis The DNA fragment used as a probe was prepared by the PCR method.

First, PPDK was purified from a culture of *Microbispora thermorosea* (IFO14047) according to the method described in Japanese Patent Appln. LOP Publication No. 168375/96, and the amino acid sequence of 28 residues from the N-terminal was determined with a protein sequencer (model 473A; manufactured by Applied Biosystems). The result is shown in SEQ ID NO:3. An oligonucleotide was synthesized based on the information of the N-terminal sequence, and the frequency of usage of codons in the genus Microbispora, and the oligonucleotide was used as a 5'-primer (TACGACTTCACCGAGGGCAACAAGGAC: SEQ ID NO:4). The synthesis of the oligonucleotide was carried out using DNA Synthesizer Model 392 (Applied Biosystems).

Then, an anti-sense oligonucleotide was synthesized based on the frequency of usage of codons in the Microbispora, and the amino acid sequence of a highly conserved region (region A: M. Niersbach et al., Mol. Gen. Genet. 231, 332–336 (1992), FIG. 3) among conventionally known PPDKs (derived from *Clostridium symbiosum, Zea mays, Flaveria trinervia* etc.) and among phosphoenol pyruvate synthase and enzyme I derived from *E. coli*, and the oligonucleotide was used as a 3'-primer (GCGGTAGACGATGGCGCGCGGGTTGTCCCA: SEQ ID NO:5). This 3'-primer corresponds to a part (Trp Asp Asn Pro Arg Ala Ile Val Tyr Arg: SEQ ID NO:6) of the amino acid sequence of PPDK derived from *Clostridium symbiosum*.

Then, 0.1 $\mu$g of the genomic DNA obtained in item (1) above was mixed with 1 pmol each of the 5'- and 3'-primers, and PCR was carried out using DNA Thermal Cycler (Perkin Elmer) and KOD DNA polymerase (TOYOBO), and as a result, a DNA fragment of about 650 bp was amplified. This PCR fragment was subjected to agarose gel electrophoresis, then purified using GENE CLEAN II (Funakoshi) and inserted into a SmaI site in plasmid pUC118 (Takara Shuzo). The nucleotide sequence of said PCR product was determined with ABI PRISM Dye Terminator Cycle Sequencing Ready Reaction Kit (Applied Biosystems), and it was thereby confirmed that said PCR product had a nucleotide sequence corresponding to a part of the PPDK gene. The PCR product was labeled with digoxigenin using DIG-Labeling Kit (Boehringer Mannheim).

The genomic DNA was completely digested with restriction enzyme BamHI or BglII and then subjected to agarose gel electrophoresis, and the DNA fragment in the gel was transferred onto a nylon membrane filter (Hybond-N+, Amersham).

Then, it was subjected to Southern blotting with the above PCR product as a probe, and it was thereby confirmed that the BamHI and BglII fragments were about 3 kb and about 7.5 kb long, respectively.
(3) Preparation of a Genomic DNA Library 10 $\mu$g of the genomic DNA was completely digested with restriction enzyme BamHI (Takara Shuzo), and the digested DNA was subjected to 0.7% agarose gel electrophoresis. Then, a gel containing the BamHI fragment of about 3 kb in length was cut out. The DNA fragment in the gel was recovered using GENE CLEAN II (Funakoshi), and about 1 $\mu$g of the BamHI fragment was obtained. Separately, 1 $\mu$g plasmid pUC118 (Takara Shuzo) was cleaved with BamHI and then dephosphorylated with *E. coli*-derived alkaline phosphatase (Takara Shuzo). 1 $\mu$g of the BamHI fragment thus obtained was ligated to pUC118 cleaved with BamHI and used to transform *E. coli* TG1 (Amersham) according to the D. M. Morrison method to give about 10,000 colonies of recombinant *E. coli* (referred to hereinafter as "BamHI library"). The *E. coli* colonies were transferred onto a nylon membrane filter (Hybond-N+, Amersham).

Similarly, about 10,000 colonies of *E. coli* TG1 with a plasmid having a BglII fragment of about 7.5 kb inserted into a BamHI site in pUC118 were obtained (referred to hereinafter as "BglII library") and transferred onto a nylon membrane.
(4) Isolation of the PPDK Gene by Colony Hybridization The PPDK gene was obtained by screening the genomic DNA libraries prepared in (3), using the probe prepared in (2). This screening was carried out using colony hybridization, and several positive colonies were obtained from the BamHI and BglII libraries, respectively.

One colony was selected from the positive colonies derived from the BamHI library, and a recombinant plasmid contained in the microorganism was purified using QIAGEN Plasmid Mini Kit (Funakoshi). This recombinant plasmid was designated plasmid pPDK21 (in which a BamHI fragment of about 3 kb is contained).

Similarly, a recombinant plasmid contained in one of the positive colonies derived from the BglII library was purified, and this recombinant plasmid was designated plasmid pPDK8 (in which a BglII fragment of about 7.5 kb is contained).
(5) Analysis of the PPDK Gene The PPDK gene in the BamHI fragment contained in plasmid pPDK21 was sequenced, and the PPDK gene in the BglII fragment contained in pPDK8 was also sequenced.

The result indicated that the 5'- and 3-side sequences of the PPDK gene are contained, respectively, in the BamHI and BglII fragments, and both of the fragments overlap in part with each other, and it was revealed that a combination of the two fragments contains the whole-length PPDK gene.

The PPDK gene had a 2,634 bp coding region (SEQ ID NO:1) and coded for 878 amino acids (SEQ ID NO:1). The N-terminal amino acid of the present enzyme as determined by a protein sequencer was proline at the 2-position in SEQ ID NO:1.

(6) Preparation of Recombinant E. coli TG1 [pPDK35]

2 µg pPDK8 was digested with restriction enzymes BamHI and HindIII (Takara Shuzo) and then subjected to agarose gel electrophoresis. A DNA fragment (about 5.5 kb) in the gel was recovered using GENE CLEAN II (Funakoshi), and about 1 µg HindIII-BamHI fragment was thus obtained. The 3'-side sequence of the PPDK gene is contained in this fragment. Separately, 3 µg pPDK21 was cleaved with HindIII and then partially digested with BamHI, and 1 µg of about 6.5 fragment was thus obtained. The 5'-side sequence of the PPDK gene and the vector DNA are contained in this HindIII-BamHI fragment. These HindIII-BamHI fragments were ligated to give plasmid pPDK30 containing the whole length PPDK gene (FIG. 1).

An oligonucleotide (CGGCGAAGGAGCGT CATATGCCGAAGTACGTT: SEQ NO:7) around the initiation codon and an anti-sense oligonucleotide (GTCCGGGGGAAAAC CATATGTCATCGGGTGTCGGA: SEQ ID NO:8) around the termination codon were synthesized and used as primers. The restriction enzyme NdeI site (underlined) is integrated in the sequences of these primers. Therefore, only the coding region of the PPDK gene can be obtained by digesting the PCR product with NdeI. 1 pmol each of the two primers and the above plasmid pPDK30 (2 ng) were mixed and then subjected to PCR using DNA Thermal Cycler (Perkin Elmer) and KOD DNA polymerase (TOYOBO), whereby the whole length of the PPDK gene was amplified.

The PCR product thus obtained was digested with NdeI (Takara Shuzo) and inserted into an NdeI site in an expression vector pUTE500K' (Japanese Patent Appln. LOP Publication No. 205861/96) to give plasmid pPDK35. This plasmid can express the whole-length of the PPDK gene under the control of the lactose promoter. Then, E. coli TG1 was transformed with pPDK35 to give recombinant E. coli TG1 [pPDK35]. E. coli TG1 [pPDK35] has been deposited as FERM BP-5686 with the National Institute of Bioscience and Human-Technology, Agency of Industrial Science and Technology, Japan.

(7) Production of the Present Enzyme by the Recombinant E. coli

An overnight culture of E. coli TG1 [pPDK35] was inoculated at 2% into a LB medium (1% peptone, 0.5% yeast extract, 0.5 NaCl, pH 7.2) containing 0.2 mM IPTG and cultured at 37° C. for 6 hours under shaking. The culture was sonicated for disruption and centrifuged to remove insolubles to give a supernatant from the disrupted microorganism. The activity of PPDK in the supernatant from the disrupted microorganism was examined according to the activity measurement method described above. As a control, a supernatant from disrupted recombinant E. coli TG1 [pUTE500K'] carrying only the expression vector pUTE500K' was examined for its PPDK activity. Further, the DNA donor, Microbispora thermorosea (IFO14047), was cultured according to the method described in Japanese Patent Appln. LOP Publication No. 1683375/96, and the resulting supernatant from the disrupted microorganism was determined for its PPDK activity. The results are shown in Table 1.

TABLE 1

| Microorganism | PPDK activity of the supernatant from the disrupted microorganism (mU/ml) |
| --- | --- |
| E.coli TG1 [pPDK35] | 1,100 |
| E.coli TG1 [pUTE500K'] | 0 |
| Microbispora thermorosea (IFO 14047) | 15 |

As is evident from Table 1, the present enzyme can be efficiently produced using recombinant E. coli TG1 [pPDK35] carrying the PPDK gene.

According to the method described in Japanese Patent Appln. LOP Publication No. 168375/96, the present enzyme was purified from the supernatant from the disrupted microorganism E. coli TG1 [pPDK35] and examined for its physicochemical properties. The physicochemical properties of the present enzyme were completely the same as those of PPDK produced by Microbispora thermorosea (IFO14047) as the DNA donor.

The present invention provides the PPDK gene, and the present enzyme can be produced in a large amount in a short time.

What is claimed is:

1. An isolated and purified nucleic acid comprising at least a portion of a nucleotide sequence which encodes SEQ ID NO:2, and wherein said nucleotide sequence encodes a pyruvate orthophosphate dikinase.

2. The nucleic acid according to claim 1, wherein said nucleic acid comprises at least a portion of a nucleotide sequence as set forth in SEQ ID NO:1.

3. A recombinant DNA vector comprising DNA having the nucleotide sequence of claim 1.

4. A host cell transformed with said recombinant vector of claim 3.

5. The host cell of claim 4, wherein said host cell is an *Escherichia coli* cell.

6. An isolated and purified nucleic acid having a nucleotide sequence which encodes SEQ ID NO:2.

7. The nucleic acid according to claim 6, wherein said nucleic acid has a nucleotide sequence as set forth in SEQ ID NO:1.

8. A recombinant DNA vector comprising DNA having the nucleotide sequence of claim 6.

9. A host cell transformed with said recombinant vector of claim 8.

10. The host cell of claim 9, wherein said host cell is an *Escherichia coli* cell.

11. A method for producing pyruvate orthophosphate dikinase, comprising:
    a) providing:
        i) a recombinant DNA vector comprising DNA having at least a portion of a nucleotide sequence which encodes SEQ ID NO:2 wherein said DNA encodes a pyruvate orthophosphate dikinase, and
        ii) a host cell;
    b) inserting said recombinant vector in said host cell under conditions such that said host cell is transformed with said recombinant vector, to produce a recombinant host cell; and
    c) culturing said recombinant host cell under conditions such that pyruvate orthophosphate dikinase is produced.

12. The method of claim 11, wherein said culturing step comprises culturing said recombinant host cell in a medium.

13. The method of claim 12, further comprising the step of recovering said pyruvate orthophosphate dikinase after said culturing step.

14. The method of claim 13, further comprising the step of purifying said pyruvate orthophosphate dikinase after said recovering step.

15. The method of claim 11, wherein said nucleotide sequence comprises at least a portion of a nucleotide sequence as set forth in SEQ ID NO:1.

16. The method of claim 11, wherein said host cell is an *Escherichia coli* cell.

17. A method for producing pyruvate orthophosphate dikinase, comprising:
    a) providing:
        i) a recombinant DNA vector comprising DNA having a nucleotide sequence which encodes SEQ ID NO:2, and
        ii) a host cell;
    b) inserting said recombinant vector in said host cell under conditions such that said host cell is transformed with said recombinant vector, to produce a recombinant host cell; and
    c) culturing said recombinant host cell under conditions such that pyruvate orthophosphate dikinase is produced.

18. The method of claim 17, wherein said culturing step comprises culturing said recombinant host cell in a medium.

19. The method of claim 18, further comprising the step of recovering said pyruvate orthophosphate dikinase after said culturing step.

20. The method of claim 19, further comprising the step of purifying said pyruvate orthophosphate dikinase after said recovering step.

21. The method of claim 17, wherein said DNA has a nucleotide sequence as set forth in SEQ ID NO:1.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 2634 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Microbispora thermorosea (B) STRAIN: IFO 14047

(ix) FEATURE:
    (A) NAME/KEY: CDS
    (B) LOCATION: 1..2634

(xi) SEQUENCE DESCRIPTION: SEQ ID NO:1:

```
ATG CCG AAG TAC GTT TAC GAC TTC ACC GAG GGG AAC AAG GAC CTC AAA      48
Met Pro Lys Tyr Val Tyr Asp Phe Thr Glu Gly Asn Lys Asp Leu Lys
 1               5                  10                  15

GAT CTG CTC GGT GGC AAG GGT GCC AAT CTG GCG GAA ATG ACC AAC ATC      96
Asp Leu Leu Gly Gly Lys Gly Ala Asn Leu Ala Glu Met Thr Asn Ile
                20                  25                  30

GGC CTT CCG GTG CCT CCC GGC TTC ACG ATC ACG ACC GAG GCC TGC CGC     144
Gly Leu Pro Val Pro Pro Gly Phe Thr Ile Thr Thr Glu Ala Cys Arg
            35                  40                  45

CAC TAT CTC CAG CAC GGT GGC ATG CCC GAT GGG CTG GCG GAG GAG ATT     192
His Tyr Leu Gln His Gly Gly Met Pro Asp Gly Leu Ala Glu Glu Ile
        50                  55                  60

GAC GAG CAC CTT GCC GCC CTC GAG GAG CGG ATG GGC AAG CGC CTG GGC     240
Asp Glu His Leu Ala Ala Leu Glu Glu Arg Met Gly Lys Arg Leu Gly
 65                 70                  75                  80

CAG GCG GAC GAC CCG TTG CTG GTC AGT GTG AGG TCG GGA GCC AAG TTC     288
Gln Ala Asp Asp Pro Leu Leu Val Ser Val Arg Ser Gly Ala Lys Phe
                85                  90                  95

TCG ATG CCG GGC ATG ATG GAG ACG GTC CTC AAC ATC GGC CTC AAC GAC     336
Ser Met Pro Gly Met Met Glu Thr Val Leu Asn Ile Gly Leu Asn Asp
            100                 105                 110

GAC TCG GTC GTC GGG CTG GCC AAG CAG TCG GGC AAC GAC CGC TTC GCC     384
Asp Ser Val Val Gly Leu Ala Lys Gln Ser Gly Asn Asp Arg Phe Ala
        115                 120                 125

TGG GAC TCC TAC CGC CGG CTC ATC CAG ATG TTC GGC AAG ACC GTC CTG     432
Trp Asp Ser Tyr Arg Arg Leu Ile Gln Met Phe Gly Lys Thr Val Leu
    130                 135                 140

GGC ATC GAC GGC GAG CTG TTC GAG AAC GCG ATG GAC GAG CTC AAG GGG     480
Gly Ile Asp Gly Glu Leu Phe Glu Asn Ala Met Asp Glu Leu Lys Gly
145                 150                 155                 160

GAG CGG GAC GAC ACC GAC CTC GAG GCC GCC GAC CTC CAG CGG CTG GTG     528
Glu Arg Asp Asp Thr Asp Leu Glu Ala Ala Asp Leu Gln Arg Leu Val
                165                 170                 175

GAC ACC TTC AAG CGC ATC GTC CGC GAC CAG ACC GGA CGC GAC TTC CCC     576
Asp Thr Phe Lys Arg Ile Val Arg Asp Gln Thr Gly Arg Asp Phe Pro
            180                 185                 190

GCC GAC CCC CGG GAG CAG ATG GAC CTG GCC GTC CGC GCG GTC TTC GAC     624
Ala Asp Pro Arg Glu Gln Met Asp Leu Ala Val Arg Ala Val Phe Asp
        195                 200                 205

TCC TGG AAC GCC CCG CGC GCG ATC CTC TAC CGG CGC CAG GAA CGC ATC     672
Ser Trp Asn Ala Pro Arg Ala Ile Leu Tyr Arg Arg Gln Glu Arg Ile
    210                 215                 220

CCC GCC GAC CTC GGC ACC GCC GTC AAC GTC GTC GCC ATG GTG TTC GGC     720
Pro Ala Asp Leu Gly Thr Ala Val Asn Val Val Ala Met Val Phe Gly
225                 230                 235                 240

AAC ATG GGC CCC GAC TCG GGC ACC GGC GTG GCC TTC ACC CGC GAC CCC     768
Asn Met Gly Pro Asp Ser Gly Thr Gly Val Ala Phe Thr Arg Asp Pro
                245                 250                 255

GGC TCG GGA CGC CAG GGC GTC TAC GGC GAC TAC CTG CGC AAC GCC CAG     816
Gly Ser Gly Arg Gln Gly Val Tyr Gly Asp Tyr Leu Arg Asn Ala Gln
            260                 265                 270

GGT GAG GAC GTC GTC GCC GGC ATC CGC AAC ACC ATC CCC CTG CAG GAG     864
Gly Glu Asp Val Val Ala Gly Ile Arg Asn Thr Ile Pro Leu Gln Glu
        275                 280                 285
```

```
CTG GAG AGC ATC AAC CCG CAG GCC TAC CGC GAG CTC CTG GAC ATC ATG    912
Leu Glu Ser Ile Asn Pro Gln Ala Tyr Arg Glu Leu Leu Asp Ile Met
        290                 295                 300

GCG ACC CTG GAG CGG CAC TAC CGC GAC CTG TGC GAC ATC GAG TTC ACG    960
Ala Thr Leu Glu Arg His Tyr Arg Asp Leu Cys Asp Ile Glu Phe Thr
305                 310                 315                 320

ATC GAG CGC GGC AAG CTG TGG ATG CTG CAG ACC CGG GTC GGC AAG CGC    1008
Ile Glu Arg Gly Lys Leu Trp Met Leu Gln Thr Arg Val Gly Lys Arg
                325                 330                 335

ACG GCC GAG GCC GCG TTC CGC ATC GCC ACC CAG CTC GTG GAC GAG GGC    1056
Thr Ala Glu Ala Ala Phe Arg Ile Ala Thr Gln Leu Val Asp Glu Gly
        340                 345                 350

CTG ATC GAC ATG GAC GAG GCG GTC GCC CGG GTC ACC GGC GAC CAG CTC    1104
Leu Ile Asp Met Asp Glu Ala Val Ala Arg Val Thr Gly Asp Gln Leu
        355                 360                 365

GCC CAG CTC ATG TTC CCC CGG TTC GCG GCG ACG GCG GAC GCC CGG AGG    1152
Ala Gln Leu Met Phe Pro Arg Phe Ala Ala Thr Ala Asp Ala Arg Arg
        370                 375                 380

CTG ACC ACC GGA ATG AAC GCC TCC CCG GGG GCC GCC GTG GGC AAG GCC    1200
Leu Thr Thr Gly Met Asn Ala Ser Pro Gly Ala Ala Val Gly Lys Ala
385                 390                 395                 400

GTC TTC AGC TCG GAG CGG GCC GTC GAA CTG GCT GGC CAG GGC GAG GCG    1248
Val Phe Ser Ser Glu Arg Ala Val Glu Leu Ala Gly Gln Gly Glu Ala
                405                 410                 415

GTC ATC CTC GTA CGG CGC GAG ACC AAC CCC GAC GAC CTC GCC GGG ATG    1296
Val Ile Leu Val Arg Arg Glu Thr Asn Pro Asp Asp Leu Ala Gly Met
                420                 425                 430

ATC GCC GCC CGG GGC GTG CTC ACC TCC AGG GGC GGC AAG ACC TCC CAC    1344
Ile Ala Ala Arg Gly Val Leu Thr Ser Arg Gly Gly Lys Thr Ser His
        435                 440                 445

GCC GCC GTC GTG GCC CGC GGC ATG GGC AAG ACC TGC GTG TGC GGG GCC    1392
Ala Ala Val Val Ala Arg Gly Met Gly Lys Thr Cys Val Cys Gly Ala
        450                 455                 460

GAG GAA CTG GAA GTG GAC CCG CAC GCC CGC CGC TTC ACC GCG CCC GGC    1440
Glu Glu Leu Glu Val Asp Pro His Ala Arg Arg Phe Thr Ala Pro Gly
465                 470                 475                 480

GGG ATC GTC GTG AAC GAG GGC GAG GTG ATC TCG ATC GAC GGA AGC ACC    1488
Gly Ile Val Val Asn Glu Gly Glu Val Ile Ser Ile Asp Gly Ser Thr
                485                 490                 495

GGG GCC GTG TAC CTC GGC GAG GTC CCG GTC ACC GCC TCG CCG GTC GCC    1536
Gly Ala Val Tyr Leu Gly Glu Val Pro Val Thr Ala Ser Pro Val Ala
                500                 505                 510

AGG TAC TTC GAG GGC GAG CCC GCC GAG GAC GAG CTG GTC CGG GCC GTC    1584
Arg Tyr Phe Glu Gly Glu Pro Ala Glu Asp Glu Leu Val Arg Ala Val
        515                 520                 525

GAC CGG ATC ATG ACC CAC GCC GAC TCC GTG CGC AGG CTC GCC GTA CGG    1632
Asp Arg Ile Met Thr His Ala Asp Ser Val Arg Arg Leu Ala Val Arg
530                 535                 540

GCC AAC GCC GAC ACG CCC GAG GAC GCC GCC CGC GCC CGC CGC TAC GGC    1680
Ala Asn Ala Asp Thr Pro Glu Asp Ala Ala Arg Ala Arg Arg Tyr Gly
545                 550                 555                 560

GCG CAG GGC ATC GGG CTG TGC CGT ACG GAG CAC ATG TTC CTG GGC GAG    1728
Ala Gln Gly Ile Gly Leu Cys Arg Thr Glu His Met Phe Leu Gly Glu
                565                 570                 575

CGG CGG CGG CTC GTG GAG GAC CTG ATC CTC GCC GCG ACC CCC GAG GAG    1776
Arg Arg Arg Leu Val Glu Asp Leu Ile Leu Ala Ala Thr Pro Glu Glu
                580                 585                 590

CGG CAG GCG GCG CTC GAC GCG CTC GAA CCC CTG CAG ACC GAA GAC TTC    1824
Arg Gln Ala Ala Leu Asp Ala Leu Glu Pro Leu Gln Thr Glu Asp Phe
```

-continued

```
          595                 600                 605
ACC GGG ATC TTC ACG GCC ATG CGC GGG CTG CCG GTG ACG ATC CGG CTG      1872
Thr Gly Ile Phe Thr Ala Met Arg Gly Leu Pro Val Thr Ile Arg Leu
        610                 615                 620

ATC GAC CCG CCG CTG CAC GAG TTC CTG CCC GAC CTC ACC GAG CTC GCG      1920
Ile Asp Pro Pro Leu His Glu Phe Leu Pro Asp Leu Thr Glu Leu Ala
625                 630                 635                 640

GTC AAG GTG GCC GTC GCG GGG GAG GCG GCG GAC GAC CGC GAC CGC AGG      1968
Val Lys Val Ala Val Ala Gly Glu Ala Ala Asp Asp Arg Asp Arg Arg
                645                 650                 655

CTC CTG GAG GCG GTC AAG CGG CTG CAC GAG CAG AAC CCG ATG CTC GGC      2016
Leu Leu Glu Ala Val Lys Arg Leu His Glu Gln Asn Pro Met Leu Gly
            660                 665                 670

CTG CGC GGC GTA CGG CTC GGC CTG ACG ATC CCC GGC CTG TTC GCC ATG      2064
Leu Arg Gly Val Arg Leu Gly Leu Thr Ile Pro Gly Leu Phe Ala Met
                675                 680                 685

CAG GTG CGG GCC ATC GCC GCG GCG GCG CGG CGG GTG GAG GAC GCC CGC      2112
Gln Val Arg Ala Ile Ala Ala Ala Ala Arg Arg Val Glu Asp Ala Arg
        690                 695                 700

GCG GAG ATC ATG ATC CCG CTG GTC GGC GCG GTG CAG GAG CTG GAG ATC      2160
Ala Glu Ile Met Ile Pro Leu Val Gly Ala Val Gln Glu Leu Glu Ile
705                 710                 715                 720

GTC CGT GAG GAG GCG GAG CGG ATC CTC GCC GAG GCG GGC GTG ACG GCG      2208
Val Arg Glu Glu Ala Glu Arg Ile Leu Ala Glu Ala Gly Val Thr Ala
                725                 730                 735

GCG ATC GGC ACG ATG ATC GAG GTG CCG CGG GCG GCG CTG ACG GCC GGG      2256
Ala Ile Gly Thr Met Ile Glu Val Pro Arg Ala Ala Leu Thr Ala Gly
            740                 745                 750

CAG ATC GCC GAG GCC GCG GAG TTC TTC TCG TTC GGC ACC AAC GAT CTC      2304
Gln Ile Ala Glu Ala Ala Glu Phe Phe Ser Phe Gly Thr Asn Asp Leu
        755                 760                 765

ACC CAG ATG ACC TGG GGG TTC TCC CGG GAC GAC GTG GAG AGC GCC TTC      2352
Thr Gln Met Thr Trp Gly Phe Ser Arg Asp Asp Val Glu Ser Ala Phe
770                 775                 780

TTC GGC CAG TAC CTC GAC CTG GGC GTC TTC GGC GTC TCG CCG TTT GAG      2400
Phe Gly Gln Tyr Leu Asp Leu Gly Val Phe Gly Val Ser Pro Phe Glu
785                 790                 795                 800

TCC ATC GAC CGG GAG GGC GTC GGC CGG CTG ATG CGG ATC GCG GTC GAG      2448
Ser Ile Asp Arg Glu Gly Val Gly Arg Leu Met Arg Ile Ala Val Glu
                805                 810                 815

GAG GGC AGG CGT GCC CGC CCC GGC CTC AAG CTC GGC ATC TGC GGC GAG      2496
Glu Gly Arg Arg Ala Arg Pro Gly Leu Lys Leu Gly Ile Cys Gly Glu
            820                 825                 830

CAC GGC GGG GAC CCC GAC TCG GTG CGG TTC TGC CAC GAG ATC GGC CTC      2544
His Gly Gly Asp Pro Asp Ser Val Arg Phe Cys His Glu Ile Gly Leu
        835                 840                 845

GAC TAC GTC TCC TGC TCG CCG TTC CGC ATT CCG GTG GCC CGG CTG GAG      2592
Asp Tyr Val Ser Cys Ser Pro Phe Arg Ile Pro Val Ala Arg Leu Glu
850                 855                 860

GCG GGC CGG GCG GCG CTG ACG TGC GCG GCG TCC GAC ACC CGA              2634
Ala Gly Arg Ala Ala Leu Thr Cys Ala Ala Ser Asp Thr Arg
865                 870                 875
```

(2) INFORMATION FOR SEQ ID NO:2:

(i) SEQUENCE CHARACTERISTICS:
        (A) LENGTH: 878 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Lys Tyr Val Tyr Asp Phe Thr Glu Gly Asn Lys Asp Leu Lys
 1               5                  10                  15

Asp Leu Leu Gly Gly Lys Gly Ala Asn Leu Ala Glu Met Thr Asn Ile
            20                  25                  30

Gly Leu Pro Val Pro Pro Gly Phe Thr Ile Thr Thr Glu Ala Cys Arg
        35                  40                  45

His Tyr Leu Gln His Gly Gly Met Pro Asp Gly Leu Ala Glu Glu Ile
    50                  55                  60

Asp Glu His Leu Ala Ala Leu Glu Glu Arg Met Gly Lys Arg Leu Gly
65                  70                  75                  80

Gln Ala Asp Asp Pro Leu Leu Val Ser Val Arg Ser Gly Ala Lys Phe
                85                  90                  95

Ser Met Pro Gly Met Met Glu Thr Val Leu Asn Ile Gly Leu Asn Asp
            100                 105                 110

Asp Ser Val Val Gly Leu Ala Lys Gln Ser Gly Asn Asp Arg Phe Ala
        115                 120                 125

Trp Asp Ser Tyr Arg Arg Leu Ile Gln Met Phe Gly Lys Thr Val Leu
    130                 135                 140

Gly Ile Asp Gly Glu Leu Phe Glu Asn Ala Met Asp Glu Leu Lys Gly
145                 150                 155                 160

Glu Arg Asp Asp Thr Asp Leu Glu Ala Ala Asp Leu Gln Arg Leu Val
                165                 170                 175

Asp Thr Phe Lys Arg Ile Val Arg Asp Gln Thr Gly Arg Asp Phe Pro
            180                 185                 190

Ala Asp Pro Arg Glu Gln Met Asp Leu Ala Val Arg Ala Val Phe Asp
        195                 200                 205

Ser Trp Asn Ala Pro Arg Ala Ile Leu Tyr Arg Arg Gln Glu Arg Ile
    210                 215                 220

Pro Ala Asp Leu Gly Thr Ala Val Asn Val Ala Met Val Phe Gly
225                 230                 235                 240

Asn Met Gly Pro Asp Ser Gly Thr Gly Val Ala Phe Thr Arg Asp Pro
                245                 250                 255

Gly Ser Gly Arg Gln Gly Val Tyr Gly Asp Tyr Leu Arg Asn Ala Gln
            260                 265                 270

Gly Glu Asp Val Val Ala Gly Ile Arg Asn Thr Ile Pro Leu Gln Glu
        275                 280                 285

Leu Glu Ser Ile Asn Pro Gln Ala Tyr Arg Glu Leu Leu Asp Ile Met
    290                 295                 300

Ala Thr Leu Glu Arg His Tyr Arg Asp Leu Cys Asp Ile Glu Phe Thr
305                 310                 315                 320

Ile Glu Arg Gly Lys Leu Trp Met Leu Gln Thr Arg Val Gly Lys Arg
                325                 330                 335

Thr Ala Glu Ala Ala Phe Arg Ile Ala Thr Gln Leu Val Asp Glu Gly
            340                 345                 350

Leu Ile Asp Met Asp Glu Ala Val Ala Arg Val Thr Gly Asp Gln Leu
        355                 360                 365

Ala Gln Leu Met Phe Pro Arg Phe Ala Ala Thr Ala Asp Ala Arg Arg
    370                 375                 380

Leu Thr Thr Gly Met Asn Ala Ser Pro Gly Ala Ala Val Gly Lys Ala
385                 390                 395                 400

Val Phe Ser Ser Glu Arg Ala Val Glu Leu Ala Gly Gln Gly Glu Ala
```

-continued

```
                    405                 410                 415
Val Ile Leu Val Arg Arg Glu Thr Asn Pro Asp Asp Leu Ala Gly Met
                420                 425                 430
Ile Ala Ala Arg Gly Val Leu Thr Ser Arg Gly Lys Thr Ser His
            435                 440                 445
Ala Ala Val Val Ala Arg Gly Met Gly Lys Thr Cys Val Cys Gly Ala
        450                 455                 460
Glu Glu Leu Glu Val Asp Pro His Ala Arg Arg Phe Thr Ala Pro Gly
465                 470                 475                 480
Gly Ile Val Val Asn Glu Gly Glu Val Ile Ser Ile Asp Gly Ser Thr
                485                 490                 495
Gly Ala Val Tyr Leu Gly Glu Val Pro Val Thr Ala Ser Pro Val Ala
            500                 505                 510
Arg Tyr Phe Glu Gly Glu Pro Ala Glu Asp Glu Leu Val Arg Ala Val
            515                 520                 525
Asp Arg Ile Met Thr His Ala Asp Ser Val Arg Arg Leu Ala Val Arg
        530                 535                 540
Ala Asn Ala Asp Thr Pro Glu Asp Ala Ala Arg Ala Arg Arg Tyr Gly
545                 550                 555                 560
Ala Gln Gly Ile Gly Leu Cys Arg Thr Glu His Met Phe Leu Gly Glu
                565                 570                 575
Arg Arg Arg Leu Val Glu Asp Leu Ile Leu Ala Ala Thr Pro Glu Glu
            580                 585                 590
Arg Gln Ala Ala Leu Asp Ala Leu Glu Pro Leu Gln Thr Glu Asp Phe
        595                 600                 605
Thr Gly Ile Phe Thr Ala Met Arg Gly Leu Pro Val Thr Ile Arg Leu
        610                 615                 620
Ile Asp Pro Pro Leu His Glu Phe Leu Pro Asp Leu Thr Glu Leu Ala
625                 630                 635                 640
Val Lys Val Ala Val Ala Gly Glu Ala Ala Asp Asp Arg Asp Arg Arg
                645                 650                 655
Leu Leu Glu Ala Val Lys Arg Leu His Glu Gln Asn Pro Met Leu Gly
            660                 665                 670
Leu Arg Gly Val Arg Leu Gly Leu Thr Ile Pro Gly Leu Phe Ala Met
        675                 680                 685
Gln Val Arg Ala Ile Ala Ala Ala Arg Arg Val Glu Asp Ala Arg
    690                 695                 700
Ala Glu Ile Met Ile Pro Leu Val Gly Ala Val Gln Glu Leu Glu Ile
705                 710                 715                 720
Val Arg Glu Glu Ala Glu Arg Ile Leu Ala Glu Ala Gly Val Thr Ala
                725                 730                 735
Ala Ile Gly Thr Met Ile Glu Val Pro Arg Ala Ala Leu Thr Ala Gly
            740                 745                 750
Gln Ile Ala Glu Ala Ala Glu Phe Phe Ser Phe Gly Thr Asn Asp Leu
        755                 760                 765
Thr Gln Met Thr Trp Gly Phe Ser Arg Asp Asp Val Glu Ser Ala Phe
    770                 775                 780
Phe Gly Gln Tyr Leu Asp Leu Gly Val Phe Gly Val Ser Pro Phe Glu
785                 790                 795                 800
Ser Ile Asp Arg Glu Gly Val Gly Arg Leu Met Arg Ile Ala Val Glu
                805                 810                 815
Glu Gly Arg Arg Ala Arg Pro Gly Leu Lys Leu Gly Ile Cys Gly Glu
            820                 825                 830
```

```
His Gly Gly Asp Pro Asp Ser Val Arg Phe Cys His Glu Ile Gly Leu
        835                 840                 845

Asp Tyr Val Ser Cys Ser Pro Phe Arg Ile Pro Val Ala Arg Leu Glu
        850                 855                 860

Ala Gly Arg Ala Ala Leu Thr Cys Ala Ala Ser Asp Thr Arg
865                 870                 875
```

(2) INFORMATION FOR SEQ ID NO:3:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:3:

```
Pro Lys Tyr Val Tyr Asp Phe Thr Glu Gly Asn Lys Asp Leu Lys Asp
1               5                   10                  15

Leu Leu Gly Gly Lys Gly Ala Asn Leu Ala Glu Met
            20                  25
```

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:4:

TACGACTTCA CCGAGGGCAA CAAGGAC                              27

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:5:

GCGGTAGACG ATGGCGCGCG GGTTGTCCCA                         30

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:6:

```
Trp Asp Asn Pro Arg Ala Ile Val Tyr Arg
1               5                   10
```

(2) INFORMATION FOR SEQ ID NO:7:

-continued

```
    (i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:7:

CGGCGAAGGA GCGTCATATG CCGAAGTACG TT                                     32

(2) INFORMATION FOR SEQ ID NO:8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:8:

GTCCGGGGGA AAACCATATG TCATCGGGTG TCGGA                                  35
```